United States Patent [19]

Gold et al.

[11] 4,052,383
[45] Oct. 4, 1977

[54] N-DIPHENYLALKYL-2-BENZYL AZACYCLIC COMPOUNDS

[75] Inventors: Elijah H. Gold, West Orange; Daniel M. Solomon, Edison, both of N.J.

[73] Assignee: Schering Corporation, Kenilworth, N.J.

[21] Appl. No.: 664,607

[22] Filed: Mar. 8, 1976

Related U.S. Application Data

[63] Continuation-in-part of Ser. No. 519,396, Oct. 30, 1974, abandoned.

[30] Foreign Application Priority Data

Oct. 24, 1975 Switzerland ..................... 13915/75

[51] Int. Cl.$^2$ .................. C07D 205/04; C07D 207/06
[52] U.S. Cl. ................................ 260/239 A; 424/267; 424/274; 424/244; 260/239 B; 260/239 BF; 260/293.72; 260/293.73; 260/293.78; 260/293.84; 260/293.81; 260/293.83; 260/293.76; 260/326.47; 260/326.87; 260/326.82; 260/326.85; 260/293.75

[58] Field of Search ..................... 260/293.83, 293.78, 260/239 A, 293.72, 326.87, 326.85, 326.47, 239 B, 239 BF, 293.73, 293.84, 293.81, 293.76, 326.82; 424/267

[56] References Cited

FOREIGN PATENT DOCUMENTS 373,038  12/1963  Switzerland
843,070  8/1960  United Kingdom
1,142,030  2/1969  United Kingdom

OTHER PUBLICATIONS

Ciba, Chem. Abs. 67, 21840x, (1967).
Likhoshesov et al., Chem. Abs. 67, 90642w, (1967).
Lunsford et al., Chem. Abs. 70, 87557d, (1969).

*Primary Examiner*—Donald G. Daus
*Assistant Examiner*—Mark L. Berch
*Attorney, Agent, or Firm*—Barbara L. Cowley Renda; Bruce M. Eisen; Stephen B. Coan

[57] ABSTRACT

Novel N-diphenylalkyl-2-benzyl azacyclic compounds are disclosed which can be used as antiobesity agents. Some of these compounds also exhibit useful antimicrobial properties. Additionally, novel chemical intermediates for the synthesis of this series are provided.

17 Claims, No Drawings

N-DIPHENYLALKYL-2-BENZYL AZACYCLIC COMPOUNDS

This application is a continuation-in-part of our copending application Ser. No. 519,396, now abandoned filed Oct. 30, 1974.

This invention relates to novel pharmacologically active 1-diphenylalkyl-2-benzyl azacyclic compounds and to compositions containing same useful in the treatment of mammalian obesity. Also included are certain intermediates useful in the preparation of these novel compounds.

The compounds of this invention can be represented by the general formula

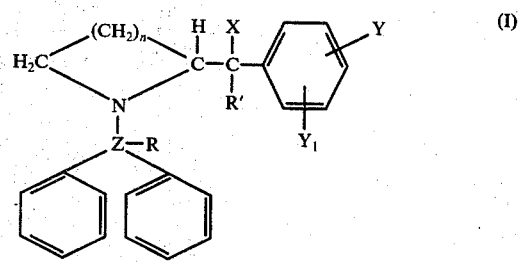

wherein $n$ is an integer from 1 to 5;

R and R' are independently selected from the group consisting of hydrogen and lower alkyl;

X is selected from the group consisting of hydrogen, $OR_2$ and $NR_1R_3$;

$R_1$ is hydrogen, lower alkyl, phenyl lower alkyl,

and

wherein $R_4$ is lower alkyl, phenyl, or phenyl lower alkyl. $R_2$ is hydrogen, lower alkyl, lower alkanoyl, benzoyl or phenyl lower alkyl;

$R_3$ is hydrogen, lower alkyl and phenyl lower alkyl;

Y and $Y_1$ are independently selected from the group consisting of hydrogen, halogen, hydroxy, lower alkoxy and trifluoromethyl;

Z is a $C_1-C_2$ alkylene group; and the pharmaceutically acceptable salts thereof.

The term "lower alkyl" as used herein and as the pertinent portion in the terms "lower alkoxy" , lower alkanoyl" and "phenyl lower alkyl" represent all alkyl groups having 1 to 4 carbon atoms such as methyl, ethyl, isopropyl, and n-butyl.

In the above phenyl groups, the phenyl ring may optionally be substituted by any of the above defined Y substituents.

The term halogen as used herein covers fluorine, chlorine and bromine.

Those compounds wherein Y and $Y_1$ represent hydrogen are preferred as antiobesity agents. It is similarly preferred that R represents a hydrogen atom and R' represents a hydrogen atom or methyl. X is preferably a hydroxy or amino group. Z is preferably methylene. The azetidine ($n=1$) is the preferred azacyclic ring.

Illustrative compounds of Formula I include the following and their stereoisomers:

1-benzhydryl-2-(α-hydroxybenzyl)azetidine;
1-benzhydryl-2-(α-aminobenzyl)azetidine;
1-benzhydryl-2-benzylazetidine;
1-benzhydryl-2-[α-hydroxy-α-methyl)benzyl]azetidine;
1-benzhydryl-2-[α-(N-acetamido)benzyl]azetidine;
1-benzhydryl-2-[α-(N-benzylamino)benzyl]azetidine;
1-[α-methylbenzhydryl]-2-hydroxybenzyl)azetidine;
1[α-ethylbenzhydryl]-2-[α-(N-acetamido)benzyl]azetidine;
1-benzhydryl-2-(α-hydroxy-m-trifluoromethylbenzyl)azetidine;
1-benzhydryl-2-(α-amino-m-trifluromethylbenzyl)azetidine;
1-benzhydryl-2-(α-methoxybenzyl)azetidine;
1-benzhydryl-2-(α-amino-p-chlorobenzyl)azetidine;
1-benzhydryl-2-(α-hydroxy-o-bromobenzyl)azetidine;
1-benzhydryl-2-[α-(N-ethylamino)benzyl]azetidine;
1-(β,β-diphenylethyl)-2-(α-hydroxybenzyl)azetidine;
1-(α-methyl-β,β-diphenylethyl)-2-(α-hydroxybenzyl)azetidine;
1-benzhydryl-2-α-benzoyloxybenzyl)azetidine,
1-benzhydryl-2-(α-benzyloxybenzyl)azetidine;
1-benzhydryl-2-[α-(N-methanesulfonylamino)benzyl]azetidine;
1-benzhydryl-2-[α-(N,N-dimethylamino)benzyl]azetidine;
1-benzhydryl-2-[α-(N-tosylamino)benzyl]azetidine;
1-benzhydryl-2-(α-hydroxybenzyl)-pyrrolidine;
1-benzhydryl-2-(α-aminobenzyl)-piperidine;
1-benzhydryl-2-(α-hydroxybenzyl)-piperidine;
1-benzhydryl-2-(α-aminobenzyl)-pyrrolidine;
1-benzhydryl-2-benzyl-pyrrolidine;
1-benzhydryl-2-(α-hydroxybenzyl)azepine;
1-benzhydryl-2-(α-hydroxybenzyl)azoeine;
1-benzhydryl-2-(α-hydroxy-3',4'-dichlorobenzyl)azetidine;
1-benzhydryl-2-(α-amino-3',4'-dichlorobenzyl)azetidine;
1-benzhydryl-2-(α-amino-3'-bromo-4'-fluorobenzyl)azetidine;
1-benzhydryl-2-(α-hydroxy-3'-chloro-5'-methoxybenzyl)azetidine;
1-benzhydryl-2-(α-amino-3',4'-dihydroxybenzyl)azetidine;
1-benzhydryl-2-(α-amino-2',4'-dihydroxybenzyl)azetidine;
1-benzhydryl-2-(α-hydroxy-3'-chloro-4'-hydroxybenzyl)azetidine;

The most preferred compound is threo-1-benzhydryl-2-(α-hydroxybenzyl)-azetidine.

The preferred acid addition salts are those formed with maleic, phthalic, succinic, tartaric, citric, malic, cinnamic, sulphuric, hydrochloric, hydrobromic, phosphoric or nitric acid.

The compounds of this invention may be prepared by standard techniques well known in the art.

Hereinafter the benzhydrylazacyclic part of the molecule is sometimes charactered by A and the phenyl ring

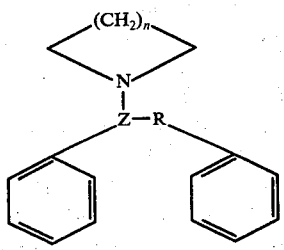

by B thus deriving at the simplified formula I for the compounds of Formula I

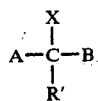  (I)

a. One process for preparing the compounds of Formula I comprises reacting a compound of the general formula

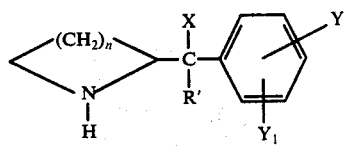  (II)

with a compound of the general formula

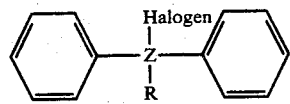  (III)

wherein the formulae $n$, R, R', X, Y and $Y_1$ are as above defined, except that any primary and secondary amino group represented by X may be protected by a protecting group which is subsequently removed.

The reaction is carried out according to known methods. Preferably the azacyclic compound (II) is dissolved in acetonitrile or another suitable solvent. Potassium bicarbonate is added and the diphenylmethylhalide (III) (e.g. bromide) is added to the resulting suspension. The mixture is refluxed (e.g. about 3 hours) and worked up in the usual manner.

b. The compounds of formula I wherein X represents OH, respectively $NH_2$ and R' is H are conveniently prepared by reducing the corresponding compounds of the general formula IV

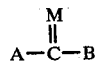  (IV)

wherein A and B are as above defined and M represents a grouping which may be reduced to X, as defined above, by standard reduction methods.

The compounds wherein X represents hydroxy are preferably prepared by reduction of the corresponding carbonyl compounds and for the preparation of compounds wherein X represents $NH_2$, M is preferably $=NH$, $=N-NH_2$ or $=N-OH$:

$(b_1)$ $(b_2)$

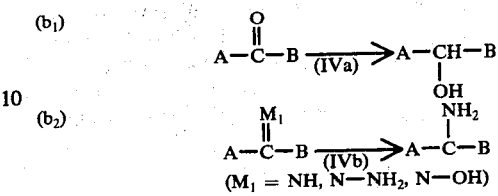

Preferably the reduction of the carbonyl compounds is carried out using sodium borohydride in methanol, ethanol or isopropanol at temperatures ranging from 0° C to 30° C. The reduction of the imine is preferably carried out by means of $LiAlH_4$ in ether at temperatures between 0° C and room temperature. Obviously, however, numerous other reducing agents and solvents may be used in the above reactions, such as $LiAlH_4$ in tetrahydrofuran (−70° C to reflux), diglyme (−70° to +80° C) or 1,2-dimethoxyethane (−70° to +80° C); $LiAlH_4$/$AlCl_3$ in the same solvents as above; $LiBH_4$ in tetrahydrofuran (~0° to +40° C), diglyme (~0° to +50° C) or ether; $NaAlH_2(OCH_2CH_2OCH_3)_2$ in benzene (+10° C to reflux), toluene (−70° to +80° C) or xylene (−70° to +80° C); $LiAlH(OC_2H_5)_3$ or $LiAlH[OC(CH_3)_3]_3$ in tetrahydrofuran or diglyme; as well as other metal hydrides, e.g. $BH_3$, $NaAlH_4$, $NaCNBH_3$, etc. The preferred temperature range is from +10° to +25° C.

Also other reduction methods such as the so-called "dissolving metal reduction" [e.g. sodium amalgam in ethanol (50°-80° C); zinc in ethanol (60°-80° C), lithium metal in liquid ammonia (−33° C)] or electrochemical or catalytic reduction may also be applied.

c. The compounds of Formula I, wherein X represents OH, or unsubstituted or mono-substituted amino and R' is lower alkyl, may conveniently be prepared by reacting the respective organometal compound with a compound of the general formula

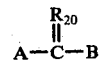

wherein $R_{20}$ is oxygen or $NR_{21}$ with $R_{21}$ being hydrogen, lower alkyl, aralkyl or acyl, followed by hydrolysis of the so-obtained organometal complex.

The suitable organometal compounds include alkyllithium and Grignard reagents such as R'MgBr or R'MgI (in ether or tetrahydrofuran at room temperature) or $Al(R')_3$ (in benzene).

d. The compounds of formula I wherein X represents a mono- or di-substituted amino group may be prepared by alkylation, aralkylation or acylation of the corresponding amino compound. The reaction is carried out according to standard alkylation, respectively acylation methods, e.g.

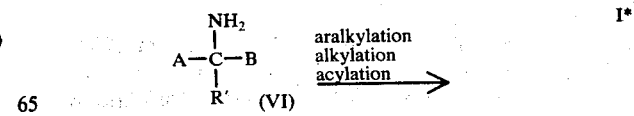  I* e. Compounds of formula I wherein X represents $NH_2$ may also be prepared from the corresponding compound having the amino group protected by one or two protecting groups by removal of said protecting group(s). The protecting groups may be any group suitable for this purpose. Preferably the amino group is protected by an acyl group such as trifluoroacetyl, e.g.

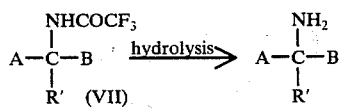

f. The compounds of formula I wherein X represents alkoxy or aralkoxy may conveniently be prepared from the corresponding hydroxy compound by standard etherification reactions:

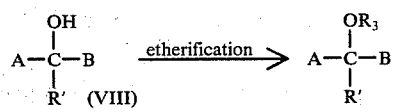

g. Compounds of formula I wherein X represents hydroxy and R' represents lower alkyl may be prepared according to standard reactions from the corresponding alkylidene compound through addition of the elements of water to the double bond:

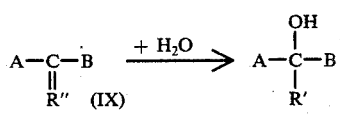

Preferably the addition reaction is carried out by treating compound (IX) with Hg(OAc)$_2$ in a mixture of tetrahydrofuran and water. R'' obviously represents a lower alkylidene group.

h. Compounds of formula I wherein X represents hydroxy and R' is hydrogen may also be prepared by the following reaction:

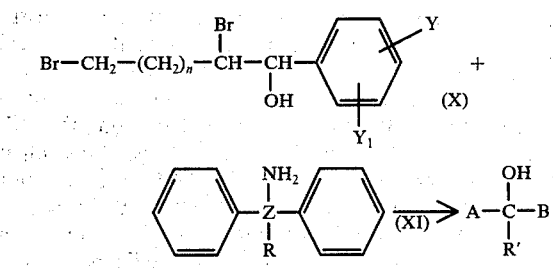

Standard reaction conditions for condensing an amine with a dibromide may be applied.

i. Compounds of Formula I wherein R represents H and Z is methylene may be prepared by the following reaction:

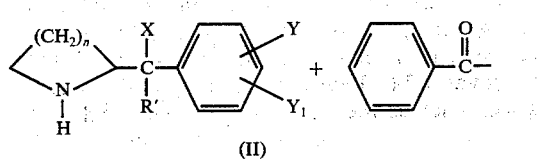

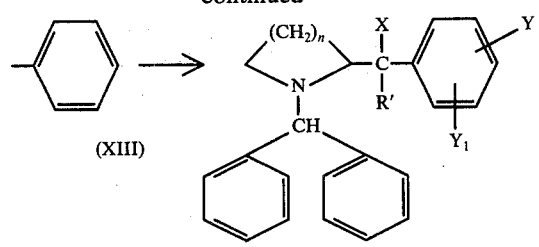

Also this reaction may be carried out according to standard methods well known in the art. Preferably the reaction is carried out in the presence of a reducing agent such as NaCNBH$_3$.

j. The compounds of Formula I wherein X represents hydrogen may be prepared by reduction of the corresponding derivatized hydroxy compound or ketone according to standard methods:

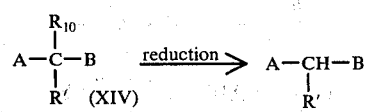

wherein in Formula XIV R$_{10}$ is a derivatized hydroxy group such as —OSO$_2$—CH$_3$ or

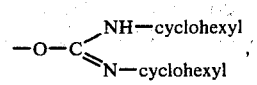

or together with R' a derivatized keto group such as a hydrazone. In th latter case R' in the final compound is hydrogen. Preferably the reduction is carried out by means of a reducing agent such as those described in process (b) above.

The starting compounds for the various processes (a) to (i) above are either well known compounds or may be prepared by standard methods well known in the art. Some of the final compounds are also starting compounds for the preparation of other final compounds.

1. Preparation of the starting compound (IVb) used in process (b):

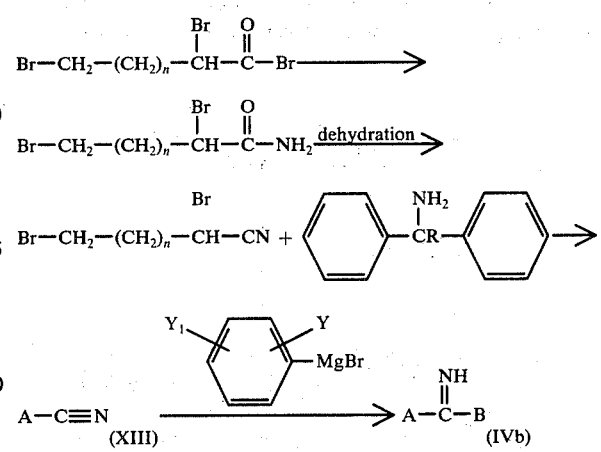

Compounds XIII and IVb are novel compounds which form part of the claimed subject matter of this application.

2. Preparation of the starting compound (IVa) used in process (b):

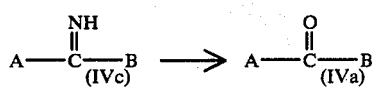

3. Preparation of the starting compound (IVb) used in process (b):

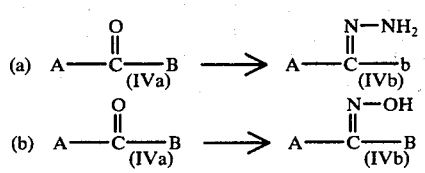

Reaction 3(a) is preferably carried out by heating the carbonyl compound (IVa) with NH$_2$NH$_2$ to reflux temperature in n-butanol and reaction 3(b) by heating (IVa) with NH$_2$OH.HCl to reflux in ethanol in the presence of either NaOH or Na$_2$CO$_3$.

4. The starting compounds of formula II [process (a)]may be maybe obtained by the following process:

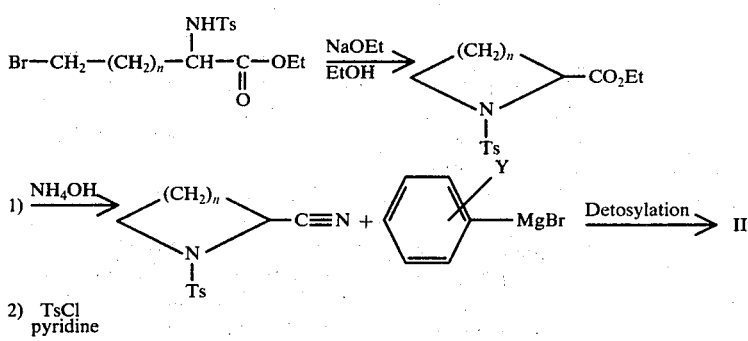

5. The starting compounds of formula VII [process (e)] wherein R' represents lower alkyl may be prepared according to the following sequence of reactions:

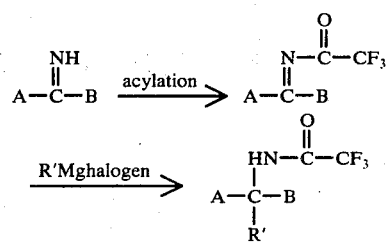

In this example the amino blocking group is trifluoroacetyl, but other hydrolysable blocking groups would also be suitable.

6. Compounds IX used in process (g) above may be prepared by a Wittig reaction as follows:

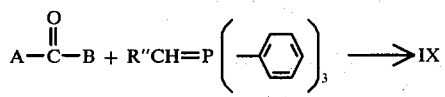

(R" represents either H or C$_1$ to C$_3$ lower alkyl)

The reaction is preferably carried out in ether at reflux temperature. The Wittig reagent is prepared in usual manner:

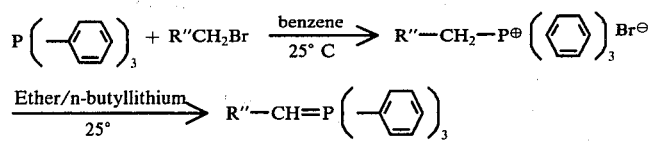

7. The starting compound X in reaction (n) may equally be prepared by standard reactions:

$$Br-CH_2-(CH_2)_n-\overset{Br}{\underset{|}{CH}}-\overset{O}{\underset{\|}{C}}-Br \xrightarrow[AlCl_3]{benzene}$$

$$Br-CH_2-(CH_2)_n-\overset{Br}{\underset{|}{CH}}-\overset{O}{\underset{\|}{C}}-\text{Ph} \xrightarrow[0°C]{NaBH_4 \atop Methanol} X$$

The compounds of formula I and their salts produce a weight loss in mammals. It is wellknown that amphetamine and other sympathomimetics have both anorexigenic activity and CNS (central nervous system) effects. The latter, i.e. the CNS effects, include nervousness, hyperexcitability, insomnia, euphoria and habituation. Amphetamine can also produce CV (cardiovascular) effects such as palpitation, tachycardia and elevation of blood pressure. Furthermore, it is well known that the sympathomimetics, on continuing administration of a given daily dose, produce a smaller anorexigenic effect with time.

The compounds of this invention are suitable for the treatment of mammalian obesity by decreasing the utilization of carbohydrate for fat synthesis, thereby decreasing excess body fat and excess body weight. Additionally, many of the compounds of the invention produce an anorectic effect without the deleterious side effects of amphetamine and other sympathomimetics.

Compositions having as active ingredients compounds of this invention exhibit an antilipogenic activity. Many have an anorexigenic activity with little or no CNS side effects, e.g. insomnia, nervousness, hyperexcitability, euphoria and habituation. Based upon laboratory tests and procedures, the effective dosage ED$_{50}$ of the active ingredient according to the present invention should be considered to be within the range of from 0.2 to 20 mg/kg p.o. of mammalian body weight per day. Thus the dosage range can be from about 15 to 1400 mg. per 70 kg. per day. A minimum effective dosage for threo-1-benzhydryl-2-(α-hydroxybenzyl)-azetidine is 0.5–3 mg/kg, whereas the LD$_{50}$ of said compound in mice is 2350 mg/kg. The daily dosage is preferably administered in divided dosages at or about meal time. The exact dose to be administered would depend upon the particular species of drug within the above range, as well as upon the dosage form and the age and weight of the mammal involved.

The compositions of the invention may be administered alone or combined with other medicinals. The compositions are administered orally. In any event a suitable pharmaceutical carrier is employed, with the carrier selected according to the physical properties of the compound in the pharmaceutic composition. The carrier should not react chemically with the compound to be administered. The preparations containing the active ingredients may be in the form of tablets, capsules, syrups, elixirs, suspensions and the like, including sustained release formulations.

Those compounds of Formula I wherein X is an amino group and Y is halogen or trifluoromethyl also exhibit interesting broad spectrum antimicrobial properties. In particular they show antibacterial and antifungal activity against such pathogenic organisms as Staphylococcus aureus, Streptococcus pyogenes C., bacillus subtilis, Candida albicans, saccharomyces cerevisiae and nocardia asteroides. Preferred compounds within this subclass are those of Example 6 below. They may be used as topical antibacterial and antifungal agents in the standard manner using conventional dermatologically acceptable vehicles. Concentrations of 0.2 to 2% are contemplated.

PREPARATIONS a. 2,4-Dibromobutyramide

Cool to $-55°$ a two-phase system, consisting of 650 ml. of concentrated ammonium hydroxide and 750 ml. of ether. Add to this stirred mixture 300 g of 2,4-dibromobutyryl bromide, (G. Bischoff, Chemical Abstracts 44 P2,549d) while maintaining the temperature between $-55°$ and $-35°$ C. Upon completion of the addition of the acid bromide, allow the stirred mixture to warm to 0° C and add sufficient ether to dissolve any suspended solid. Separate the layers and extract the aqueous phase twice with ether. Wash the combined ether phases sequentially with water and brine (saturated aqueous sodium chloride), and dry the solution over anhydrous sodium sulfate. Remove the bulk of the solvent in vacuo, leaving a thick suspension. Add hexane to this suspension and triturate thoroughly. Filter to obtain the analytically pure title amide, m.p. 80.5°–81.5° C.

b. 2,4-Dibromobutyronitrile

Prepare a mixture of 100 g of 2,4-dibromobutyramide and 76.5 g of phosphorous pentoxide. Place the solid mixture under a vacuum of 0.02–0.10 Torr, heat to 200° C, and collect distillate until a head temperature of 120° C is reached. Dissolve this crude distillate in ether and wash sequentially with 10% HCl, aqueous sodium bicarbonate, water and brine. Dry the ether solution over anhydrous magnesium sulfate and remove the solvent in vacuo. Vacuum distill the residual oil through a fractionating column and collect the analytically pure title compound at 66°–67° C at 0.05 Torr.

c. 1-Benzhydryl-2-cyanoazetidine

Reflux for 18 hours, a stirred mixture of 10 g of 2,4-dibromobutyronitrile, 7.35 g of benzhydrylamine, and 7.41 g of sodium bicarbonate in 100 ml of acetonitrile. Filter off the solids and remove the acetonitrile in vacuo. Treat the residue with ether and filter out insoluble solids. Wash the ether solution first with water, then with a solution of 5.40 g of oxalic acid in 200 ml of water, and finally with brine (saturated aqueous NaCl solution). Dry the solution over anhydrous magnesium sulfate and remove solvent in vacuo. Crystallize the solid residue from methylene chloride-hexane to obtain the analytically pure title compound, m.p. 103.5–105.0° C.

d. 1-Benzhydryl-2-benzimidoylazetidine

Suspend phenylmagnesium bromide in ether by adding under gentle reflux a solution of 189.2 g of bromobenzene in 500 ml of ether to a stirred suspension of 24.4 g of magnesium turnings in 1000 ml. of dry ether. Upon completion of the addition, reflux for another 30 minutes, then allow the mixture to cool for 15 minutes at room temperature. Add portionwise, over 3 to 4 minutes, 119.6 g of 1-benzhydryl-2-cyanoazetidine. Stir the mixture for 18 hours at room temperature, cool to 0° C and quench by the sequential addition of 750 ml. of water, 250 ml. of ether and 400 ml. of methylene chloride. Filter the mixture. Remove the aqueous layer of the filtrate. Wash the organic phase with water and dry over anhydrous sodium sulfate. Remove the solvent in vacuo. Triturate the solid residue with 500 ml of isopropyl ether and filter to obtain the analytically pure title product, m.p. 123.5°–126.5° C.

e. 1-Benzhydryl-2-Benzoylazetidine

Add 68 ml of 3.6N aqueous sulfuric acid to a stirred solution of 40.0 g of 1-benzhydryl-2-benzimidoylazetidine in 800 ml. of methanol. Stir under a nitrogen atmosphere for 1.5 hours at room temperature. Slowly pour the mixture, with continuous stirring, into 234 ml. of 1.1N aqueous sodium bicarbonate. Filter the resultant solid, and extract the filter cake with methylene chloride. Combine the methylene chloride extracts with the methanolic filtrate and remove all solvent in vacuo. Dissolve the residual solid in ether, wash with water, and dry over anhydrous sodium sulfate. Remove the drying agent, concentrate the solution in vacuo to a volume of 350 ml. and triturate the solid which precipitates. Filter to obtain the analytically pure product, m.p. 114°–115° C.

EXAMPLE 1

Threo-($\pm$)-1-Benzhydryl-2-($\alpha$-hydroxybenzyl)azetidine

Add 9.3 g of sodium borohydride to a stirred ice cold suspension of 40 g of 1-benzhydryl-2-benzoylazetidine in 1600 ml of methanol. When frothing subsides, allow the reaction mixture to warm to room temperature. Stir for 16 hours; then remove solvent in vacuo. Dissolve the residual solids and oil in a mixture of ether and water. Separate the layers and extract the aqueous phase with ether. Wash the combined ether extracts successively with water and saturated sodium chloride solution and dry over anhydrous sodium sulfate.

Add 40 ml. of 4N ethereal HCl to the stirred ether solution (800 ml). Decant, add 800 ml. of fresh ether, and triturate the gummy precipitate to a powdery solid. Recrystallize the crude salt from methanol-ethyl acetate to obtain the analytically pure hydrochloride salt of the title compound. m.p. 175°–176° C dec. This crystalline salt analyzes correctly for the molecular formula $NOC_{23}H_{23}$.HCl and is a mixture of predominantly threo isomer together with the erythro isomer. To prepare the free base, stir a suspension of 60 g of the hydrochloride salt in a mixture consisting of 220 ml of 1.0 N aqueous sodium bicarbonate, 500 ml of ether, and 75 ml of methylene dichloride. Separate the layers, wash the organic phase successively with water and brine, then dry over anhydrous sodium sulfate. Remove solvent in vacuo and triturate the residual solid in ether to obtain the analytically pure free base form of the title compound, m.p. 87.5°–88.5° C.

EXAMPLE 2

Optical Resolution of Threo-(±)-1-benzhydryl-2-(α-hydroxybenzyl)azetidine

Dissolve 3.50 g of racemic threo-1-benzhydryl-2-(α-hydroxybenzyl)azetidine and 3.03 g of N-tosyl-L-leucine in 30 ml of boiling acetonitrile. Allow the solution to cool to room temperature. Filter the solid and recrystallize from acetonitrile to obtain the analytically pure diastereomeric salt: m.p. 154°–155° C, $[\alpha]_D^{26}$ − 39.40° (1%. DMF). The mother liquor will be utilized to obtain the more soluble diastereomer.

Prepare the free base form of the pure diastereomeric salt in the conventional manner by treatment with aqueous sodium carbonate and ether. Recrystallize the solid thus obtained from isopropyl ether to obtain one analytically pure enantiomeric free base form of the title compound: m.p. 72°–73° C, $[\alpha]_D^{26}$ − 54.80° (1%, EtOH). To obtain the hydrochloride, dissolve the pure free base in ether, treat with ethereal hydrogen chloride, and filter the precipitate. Triturate the solid with ethyl acetate to obtain the analytically pure dextrorotatory hydrochloride salt of the title compound: m.p. 149°–152° C, $[\alpha]_D^{26}$ + 91.1° (1%, DMF). Prepare, by treatment with sodium carbonate and ether, the free base from the mother liquor derived from the formation and recrystallization of the N-tosyl-L-leucine salt described above. Dissolve 2.0 g of this free base and 1.73 g of N-tosyl-D-leucine in 30 ml. of boiling acetonitrile. Allow the solution to cool to room temperature. Filter the solid and recrystallize from acetonitrile to obtain the analytically pure diastereomeric salt, m.p. 155°–156° C, $[\alpha]_D^{26}$ = +40.20° (1%, DMF). Prepare the free base of this salt by treatment with aqueous sodium carbonate and ether. Recrystallize the resultant solid from isopropyl ether to obtain the analytically pure dextro enantiomeric free base form of the title compound: m.p. 72°–73° C, $[\alpha]_D^{26}$ + 55.30° (1%, EtOH). Dissolve the pure free base in ether, treat with ethereal hydrogen chloride, and filter the precipitate. Triturate the solid with ethyl acetate to obtain the analytically pure levo enantiomeric hydrochloride salt of the product of this example: m.p. 150°–151° C, $[\alpha]_D^{26}$ −92.1°, (1%, DMF). Other salts may be prepared by treating the free base with an acid in conventional manner to form the pharmaceutically acceptable acid addition salts.

EXAMPLE 3

Erythro-1-Benzhydryl-2-(α-hydroxybenzyl)azetidine

Add 75.0 g of 1-benzhydryl-2-benzoylazetidine in several portions to a stirred solution of 10.0 g of lithium borohydride in 3 liters of ether. Allow the resultant solution to stand overnight at room temperature. Add one liter of water and sufficient methylene chloride to solubilize any insoluble organic material. Separate the layers and wash the organic phase with water. Dry over anhydrous sodium sulfate. Remove solvent in vacuo, then redissolve the residual solid in 2 liters of dry ether. Add 85 ml of 3.5N ethereal hydrogen chloride. Filter the solid and recrystallize from methanol-ethyl acetate to obtain the analytically pure hydrochloride salt of the title compound, m.p. 182.5°–184.0° C.

To prepare the free base, stir a suspension of 50 g of the hydrochloride salt in a mixture of 175 ml of 1.1N aqueous sodium bicarbonate, 400 ml of ether and 50 ml of methylene chloride. Separate the layers and wash the organic phase successively with water and brine. Dry over anhydrous sodium sulfate. Remove solvent and triturate the residual solid in ether to obtain the analytically pure base form of the title compound, m.p. 130.5°–131.0° C. Other salts may be prepared in conventional manner by treating the free base with an acid to form the pharmaceutically acceptable acid addition salts.

EXAMPLE 4

1-Benzhydryl-2-(α-aminobenzyl)azetidine

Add 5.0 g of 1-benzhydryl-2-benzimidoylazetidine to an ice cold suspension of 1.16 g of lithium aluminum hydride in 135 ml of dry ether. Stir the mixture at 0° C for 15 minutes, then allow the mixture to warm to room temperature and continue stirring for 18 hours. Cool the suspension to 0° C and cautiously quench by the successive addition of 1.25 ml of water, 1.75 ml of 10% aqueous sodium hydroxide, and 3.5 ml of water. Stir, filter and wash the precipitate with ether. Combine the ether washes with the original filtrate and wash the resultant solution successively with water and brine. Dry over anhydrous sodium sulfate, and remove ether in vacuo.

The Erythro-isomer

Recrystallize the residual solid from isopropyl ether to obtain the analytically pure erythro-isomer of the title compound, m.p. 112.5°–113° C. (Retain the mother liquor for the isolation of the threo-isomer.)

To prepare the dihydrochloride salt of the erythro-isomer, dissolve 3.5 g of the pure free base in 80 ml of ether. Add 5 ml of 5N ethereal hydrogen chloride. Filter the precipitate and wash with ether to obtain the analytically pure dihydrochloride salt, containing 0.5 mole of water of crystallization. The melting point shows a broad decomposition range around 190° C.

The threo-isomer

Remove in vacuo the isopropyl ether from the mother liquor of the crystallization of the erythro-isomer free base. Chromatograph the residual oil on silica gel, eluting with 1/5 (volume/volume) ethyl acetate-hexane, to obtain the analytically pure free base form of the threo-isomer of the title compound, m.p. 101°–102° C.

To prepare the dihydrochloride salt of the threo-isomer dissolve 4.5 g of the pure free base in 110 ml of ether and add 6.5 ml of 5N ethereal hydrogen chloride. Filter the precipitate and triturate in ether to obtain the analytically pure dihydrochloride salt, containing one mole of water of crystallization, m.p.: decomp. over a broad range beginning at 142° C.

Optical Resolution of Erythro-(±)-1-benzhydryl-2-(α-aminobenzyl)azetidine a. Dissolve 9.84 of racemic erythro-1-benzhydryl-2-(α-aminobenzyl)azetidine and 11.58 g of di-p-toluyl-1-tartaric acid in 200 ml of boiling acetonitrile. Allow the solution to cool to room temperature and decant off the fine powdery solid present. From acetonitrile, recrystallize the large dense crystals that remain, to obtain the analytically pure diastereomeric salt: m.p. 126°–128° C $[\alpha]_D^{26}$ + 17.1° (1% EtOH). Dissolve the pure free base in ether and treat the solution with ethereal hydrogen chloride. Filter and wash the precipitate with cold acetonitrile to obtain the analytically pure enantiomeric hydrochloride salt of this example: m.p. 190°–192° C$[\alpha]_D^{26}$ +8.2° (1% H$_2$O).

b. Dissolve 9.84 g of racemic erythro-1-benzhydryl-2-(α-aminobenzyl)azetidine and 11.58 g of d-p-toluoyl-d-tartaric acid in 200 ml of boiling acetonitrile. Allow the solution to cool to room temperature and decant off the fine powdery solid present. From acetonitrile, recrystallize the large, dense crystals that remain to obtain the analytically pure diastercomeric salt: m.p. 125°–128° C $[\alpha]_D^{26}$ −17.4° (1% DMF). Prepare the free base from this salt by treatment with aqueous sodium hydroxide and ether. Triturate the solid thus isolated with petroleum ether to obtain the analytically pure enantiomeric free base form of the title compound: m.p. 90°–92° C $[\alpha]_D^{26}$ −118.6° (1% EtoH). Dissolve the pure free base in ether and add ethereal hydrogen chloride to the solution. Filter and wash the precipitate with cold acetonitrile to obtain the analytically pure enantiomeric hydrochloride salt of this example: m.p. 191°–192° C $[\alpha]_D^{26}$−8.5 (1% H$_2$O).

EXAMPLE 5

A:
1-Benzhydryl-2-(m-trifuoromethylbenzimidoyl)azetidine

Suspend m-trifluoromethylphenylmagnesium bromide in ether by adding a solution of 18 g of m-bromobenzotrifluoride in 30 ml of ether to a stirred suspension of 1.94 g of magnesium turnings in 20 ml of dry ether. Upon completion of addition, allow the reaction mixture to cool to room temperature and add 7.95 g of 1-benzhydryl-2-cyanoazetidine. Stir the mixture for 18 hours at room temperature, cool to 0° C or lower, and quench by the dropwise addition of 50 ml of water. Add 15 ml of ether and 25 ml of mthylene chloride and filter the mixture through a pad of diatomaceous earth, such as commercially available Celite. Remove the aqueous layer of the filtrate. Wash the organic phase with water and dry over anhydrous sodium sulfate. Remove the solvent in vacuo to obtain the title compound as an oil. By suitable substitution, analogous halo compounds can be prepared.

B:
1-Benzhydryl-2-(m-trifluoromethylbenzolyl)azetidine

Stir at room temperature for 45 minutes a solution of 1.0 g of 1benzhydryl-2-(m-trifluoromethyl)benzimidoylazetidine from step A and 3.6N aqueous sulfuric acid in 20 ml of methanol. Add 5 ml of 1.1N aqueous sodium bicarbonate to the reaction mixture, and remove methanol in vacuo and obtain the title compound as an oil.

C:
1-Benzhydryl-2-(α-hydroxy-m-trifluromethylbenzyl)-azetidine

Add 910 mg of sodium borohydride to a solution of 4.75 g of 1-benzhydryl-2-(m-trifluromethyl)benzoylazetidine obtained by reaction B in 15 ml of methanol and stir the resultant mixture at room temperature for 3.5 hours. Remove methanol in vacuo. Dissolve the residue in ether and water, separate into layers, and wash the ether phase successively with water and brine. Dry over anhydrous magnesium sulfate. Remove the solvent in vacuo and chromatograph the residual oil on 85 g of silica gel, using 1/14 (v/v) ethyl acetate-hexane as eluant, to obtain the free base forms of the erythro and threo isomers of the title compound. Crystallize, from ether, the oil corresponding to the first-eluted chromatographic fraction to obtain the free base form of the erythro-isomer of the title compound, m.p. 145.0°–145.5° C.

Dissolve, in 60 ml of ether, the oil corresponding to the second chromatographic fraction and treat the solution with 2.5 ml of 5N ethereal hydrogen chloride. Triturate the precipitate. Filter and recrystallize the solid from methanol-ethyl acetate to obtain the analytically pure hydrochloride salt of the threo-isomer of this example: m.p. 144°–146° C (decomp.).

EXAMPLE 6

1-Benzhydryl-2-(α-amino-m-trifluoromethylbenzyl)azetidine

Add 4.75 g of 1-benzhydryl-2-(m-trifluoromethylbenzimidoylazetidine to a stirred, ice-cooled suspension of 695 mg of lithium aluminum hydride in 85 ml of dry ether. When addition is complete, remove the cooling bath and stir the mixture at room temperature for 5 hours. Cool the suspension to 0° C and quench the excess metal hydride by the cautious successive addition of 0.9 ml of water, 1.4 ml of 10% aqueous sodium hydroxide and 2.8 ml of water. Filter and wash the precipitate with ether. Combine these washes with the original filtrate and wash the resultant solution successively with water and brine. Dry over anhydrous magnesium sulfate. Remove the ether in vacuo and chromatograph the residual oil on 105 g of silica gel, eluting with 1/8 (v/v) ethyl acetate-hexane to obtain as purified oils the free base borms of the erythro and threo-isomers of the title compound (distinguished by NMR spectra). Under the above conditions, the erythro form is the more mobile of the two isomers.

Di-HCl salt of the Erythro-isomer

Dissolve the free base form of the erythro-isomer as obtained from the above chromatography in 50 ml of ether and treat the solution with 2 ml of 5N ethereal hydrogen chloride. Filter the resultant solid and recrystallize it from methanol-acetonitrile to obtain the analytically pure dihydrochloride salt of the erythro-isomer of the title compound, m.p.: darkens and softens to a gum at 176° C, then decomposes over a broad temperature range that varies with the rate of heating.

Dihydrochloride salt of the threo-isomer

Dissolve the free base form of the threo-isomer, as obtained from the above chromatography, in 5 ml of ether and treat the solution with 1 ml of 5N ethereal hydrogen chloride. Filter the resultant solid and crystallize it from methanol-ethyl acetate to obtain the analytically pure dihyrochloride salt of the threo-isomer of the title compound, m.p. 173.5°–175.5° C (decomp.).

EXAMPLE 7

1-Benzhydryl-2-benzylazctidine

To a solution of 6.0 g of threo-1-benzhydryl-2-(α-hydroxybenzyl)-azetidine and 1.86 g of triethylamine in 100 ml of dry benzene, maintained below 10° C, add 2.08 g of methanesulfonyl chloride. Allow the stirred solution to stand at 6–10° C for 2 hours. Add to the mixture, 150 ml of dry dimethyl sulfoxide and 1.40 g of sodium borohydride. Stir at room temperature for 85 hours. Add ether and water, separate the resultant layers, and re-extract the aqueous layer with additional other. Wash the combined organic phases successively with water and brine, dry over anhydrous sodium sulfate, and remove solvent in vacuo. Chromatograph the resultant oil on 275 g of silica gel, eluting with 1/20 (v/v) ethyl acetate-hexane, to obtain the analytically pure product of this example, m.p. 87.5°–89.5° C.

EXAMPLE 8

Erythro-1-benzhydryl-2-[α-(N-acetamido)-benzyl]-azetidine

Dissolve 500 mg of erythro-1-benzhydryl-2-(α-aminobenzyl)-azetidine in 6 ml of dry ether, and to the stirred solution add 1 ml of acetic anhydride. Stir at room temperature for 5 minutes. Dissolve the resultant precipitate in 3/1 (v/v) ether-methylene chloride and wash the solution successively with 10% aqueous sodium bicarbonate, water and saturated aqueous sodium chloride solution. Dry over anhydrous sodium sulfate and remove solution in vacuo. Triturate the resultant solid with ether to obtain the analytically pure title compound, m.p. 183°–187° C.

EXAMPLE 9

A: 1-Benzhydryl-2-[α-(N-trifluoroacetylamino)benzyl]-azetidine

Dissolve 100 mg of 1-benzhydryl-2-benzimidoylacetidine in 3.5 ml of benzene, add one equivalent of triethylamine and cool the solution to approximately 5° C. Add on equivalent of trifluoroacetic anhydride and maintan the reaction solution at 5° C for 30 minutes. Treat the solution with ether and sufficient aqueous sodium bicarbonate to make the resultant mixture weakly alkaline. Separate the layers and wash the organic phase successively with water and saturated aqueous sodium chloride solution. Dry over anhydrous sodium sulfate, and remove solent in vacuo. The resultant oil is used directly without further purification in the preparation of 1-benzhydryl-2-[α-methyl-α-(N-trifluoroacetamido)-benzyl]azetidine. B: 1-Benzhydryl-2-[α-methyl-α-(N-trifluoroacetamido]-benzyl]azetidine Cool to 0° C a solution of 1.0 g. of 1-benzhydryl-2-[α-(N-trifluoroacetylimino)benzyl]azetidine (from step A) in 25 ml of ether. To this solution, add 1.3 ml of a 2 molar ethereal solution of methyllithium. Maintain the reaction mixture at 0° C for 1 hour, then allow to stand at room temperature for two hours. Cool the mixture in an ice bath and quench by careful dropwise addition of 45 ml of saturated aqueous ammonium chloride solution. Dilute the mixture with additional ether and water, separate the layers, and wash the organic phase successively with water and saturated aqueous sodium chloride solution. Dry over anhydrous sodium sulfate and remove solvent in vacuo to obtain the title compound.

C: 1-Benzhydryl-2-[α-methyl-α-amino]azetidine

Dissolve 1.0 g of 1-benzhydryl-2-[α-methylα-(N-trifluoroacetamido)benzyl]azetidine. (from step B) in 15 ml of a 1N solution of potassium hydroxide in methanol. Add 0.5 ml of water and reflux under nitrogen for 65 hours. Cool to room temperature, treat the reaction mixture with ether and water, and separate the resultant layers. Wash the organic phase thoroughly with water, then with saturated aqueous sodium chloride solution, and dry over anhydrous sodium sulfate. Remove solvent in vacuo to obtain the product of this example.

EXAMPLE 10

Threo-1-benzhydryl-2-(α-methoxybenzyl)azetidine

Cool to 0°–5° a solution of 4.0 g of threo-1-benzhydryl-2-(α-hydroxybenzyl)azetidine in 40 ml of dry dimethyl formamide. To this solution add 640 mg of a 55% (by weight) dispersion of sodium hydride and stir at ice bath temperature for 30 minutes. Add 2.25 g of methyl iodide and stir at room temperature for 2.5 hours. Quench the reaction mixture with water, add ether, and separate the layers. Wash the organic phase successively with water and saturated aqueous sodium chloride solution, dry over anhydrous sodium sulfate, and remove solvent in vacuo. Chromatograph the residual oil over silica gel, eluting with 1/25 (v/v) ethyl acetate-hexane. Low temperature crystallization from hexane of the first-eluted fraction yields the analytically pure title compound, m.p. 51°–56° C.

EXAMPLE 11

1-Benzhydryl-2-[α-methyl-α-hydroxyl)-benzyl]azetidine

By treating 1-benzhydryl-2-benzoylazetidine obtained according to preparation (e) with methyllithium in known manner, the title compound is obtained, m.p. of the HCl salt: 152°–153.5° C.

EXAMPLE 12

Threo-1-benzhydryl-2-(α-hydroxybenzyl)-azetidine

Dissolve 1.63 g of threo-2-(α-hydroxybenzyl)azetidine in 45 ml of acetonitrile. Add 1.0 g of potassium bicarbonate and to the resultant suspension add with stirring a solution of 2.57 g of benzhydryl bromide (bromodiphenylmethane) in 15 ml of acetonitrile. Heat the stirred mixture to reflux and maintain reflux under a nitrogen atmosphere for 3 hours. Allow the reaction mixture to cool, dilute with ether and filter out solids. Remove solvent (in vacuo) from filtrate. Dissolve the residue in ether, wash the solution with water and brine and dry over anhydrous sodium sulfate. To the dried ether solution add 5 ml of 2 M ethereal hydrogen chloride. Filter the resultant solid and recrystallize it from methanol-ethyl acetate to obtain the analytically pure hydrochloride salt of threo-1-benzhydryl-2-(α-hydroxybenzyl)azetidine, m.p. 175°–176° dec.

EXAMPLE 13

1-Benzhydryl-2-(α-hydroxy-α-methylbenzyl)azetidine

To a stirred solution of 3.19 g of mercuric acetate in a medium consisting of 10 ml of water and 15 ml. of tetrahydrofuran, add slowly a solution of 3.39 g. of 1-benzhydryl-2-(α-methylenebenzyl)azetidine in ca. 60 ml of tetrahydrofuran. When addition is complete, stir the reaction mixture for 30 minutes at room temperature. Add 10 ml of a 3 M aqueous solution of sodium hydroxide, followed by 10 ml. of a 0.5 M solution of sodium borohydride in 3 M sodium hydroxide and stir for 30 minutes. Dilute the reaction mixture with sufficient ether to produce a two-phase system. Separate the organic layer, dry over anhydrous sodium sulfate, and remove solvent in vacuo to obtain a mixture of erythro and threo isomers of 1-benzhydryl-2-(α-hydroxy- α- methylbenzyl)azetidine. Dissolve this product in 100 ml. of ether, and add 6 ml. of 2 M ethereal hydrogen chloride. Recrystallize the crude salt to obtain the analytically pure hydrochloride salt of one isomer (relative stereochemistry has not been definitely assigned), of the title compound with m.p. 182°–184°. Further crystallization of the mother liquor yields the hydrochloride salt of the second isomer with m.p. 152°–153.5°.

EXAMPLE 14

1-Benzhydryl-2-(α-methylaminobenzyl)azetidine

To a stirred solution of 2.50 g of 1-benzhydryl-2-(α-aminobenzyl)azetidine in 25 ml. of N,N-dimethylformamide, add 365 mg. of a 55% dispension of sodium hydride. Stir the mixture under a nitrogen atmosphere and when frothing subsides, warm and maintain the stirred mixture at 40° for twenty minutes. Cool the mixture to −25° C and add 1.20 g. of methyl iodide. Remove the reaction mixture from the cooling bath and allow it to warm to room temperature. After ca. 15 minutes at room temperature, pour the contents of the reaction flask into a stirred mixture of 100 ml. of water and 25 ml. of ether. Separate the layers and reextract the aqueous phase with ether. Combine all ether extracts, wash successively with water and brine, dry over anhydrous sodium sulfate, and strip off solvent in vacuo. Crystallize the residual solid from ether to obtain the analytically pure title compound containing ¼ mole of water-of-crystallization and having m.p. 111°–113°.

EXAMPLE 15

1-Benzhydryl-2-(α-hydroxybenzyl)azetidine

To a mixture of 5.0 g. of 1-phenyl-2,4-dibromobutanol (mixture of diastereomers) and 3.25 g. of potassium bicarbonate in 30 ml. of acetonitrile, add 2.70 g. of benzhydryl amine. Reflux the stirred mixture under a nitrogen atmosphere for 18 hrs. Filter the solids and wash them thoroughly with ether. Combine the washes with the filtrate and remove solvent in vacuo from the resultant solution. Dissolve the residue in ether and wash successively with a 1:1 mixture of brine and water, then with brine only. Dry over anhydrous sodium sulfate, and strip solvent in vacuo. Chromatograph the residue on silica gel, using 1/15 (v/v) ethyl acetate-hexane as eluants, to obtain the erythro (analytically pure has m.p. 131.0°–131.5°) and threo (analytically pure has m.p. 87.5°–88.5°) isomers of 1-benzhydryl-2-(α-hydroxybenzyl)azetidine.

EXAMPLE 16

1-Benzhydryl-2-(α-acetoxybenzyl)azetidine

Cool in an ice bath a solution of 1.5 g. of threo-1-benzhydryl-2-(α-hydroxybenzyl)azetidine and 1.22 g. of triethylamine in 15 ml. of dry benzene. To the stirred solution, add 865 g. of acetyl chloride. Stir the resultant rection mixture in the ice bath for 10 minutes, then at room temperature for 1.5 hrs. Pour the reaction mixture into a stirred mixture of 50 ml. of ether and 50 ml. of water. Separate the layers, re-extract the aqueous phases with fresh ether, and combine the ether phases. Wash the resultant ether solution successively with water and brine, dry over anhydrous sodium sulfate, and remove solvent in vacuo. Crystallize the residue from ether to obtain analytically pure 1-benzhydryl-2-(α-acetoxybenzyl)-azetidine, m.p. 128°–131°.

EXAMPLE 17

Threo-1-Benzhydryl-2-(α-hydroxybenzyl)azetidine

Dissolve 500 mg. of threo-2-(α-hydroxybenzyl)azetidine in 12.5 ml. of methanol. To the solution add 1.60 ml. of 1.9 M ethereal hydrogen chloride, then 560 mg. of benzophenone and 193 mg. of sodium cyanoborohydride. Add a quantity of type 3A molecular siever and allow the resultant mixture to stir under a nitrogen atmosphere at room temperature until reaction is complete as ascertained by thin-layer chromatography. Filter out the solids and wash thoroughly with methylene chloride. Combine the methylene chloride washes with the filtrate and pour the resultant solution into a stirred mixture of 50 ml. of saturated aqueous sodium bicarbonate solution and 35 ml. of ether. Separate the phases and re-extract the organic layers with ether. Wash the combined organic phases successively with water and brine and dry over anhydrous sodium sulfate. Filter the drying agent, remove the solvent in vacuo, and redissolve the residue in ca. 10 ml. of ether. To this ether solution, add 1.75 ml. of 2 M ethereal hydrogen chloride. Filter the resultant solid and recrystallize it from methanol-ethyl acetate to obtain the analytically pure hydrochloride salt of threo-1-benzhydryl-2-(α-hydroxybenzyl)-azetidine, m.p. 175°–176° dec.

EXAMPLE 18

Threo-1-(β,β-diphenylethyl)-2-(α-hydroxybenzyl)azetidine

Hydrogenate for 20 hrs. at 50–55 psi a mixture of 600 mg. of threo-2-(α-hydroxybenzyl)azetidine, 960 mg. of diphenylacetaldehyde, and 25 mg. of 20% palladium-on-charcoal. Filter the catalyst, remove solvent in vacuo, and crystallize the residual oil from ether. Dissolve the crystalline free base in ether, treat with a slight excess of 1.9 M ethereal hydrogen chloride, filter the resultant precipitate, and triturate this solid with fresh ether to obtain the analytically pure hydrochloride of the title compound, m.p. 159.5°–160.5° dec.

EXAMPLE 19

Erythro-(1-benzhydryl-2-(α-hydroxybenzyl)piperidine

Reflux under an inert atmosphere for 190 hrs. a stirred suspension of 1.89 g. of erythro-α-(2-piperidyl)phenylmethanol; 2.25 g. of benzhydryl bromide, and 1.00 g. of potassium bicarbonate in 100 ml. of dry acetonitrile containing 14 ml. hexamethylphosphoramide. Cool to room temperature, pour into water, and extract with ether. Wash the extract successively with water and brine and dry over anhydrous sodium sulfate. Acidify the dry ether solution with 4.4 ml. of 1.9 M ethereal HCl. Filter and wash the resultant precipitate with acetone to obtain the analytically pure hydrochloride salt of the title compound, m.p. 232.5°–234° dec.

The threo-isomer of title compound is analogously produced and upon recrystallization from methanol-ethyl acetate, the HCl salt exhibits m.p. 225.5°–227.0° dec.

Similarly, by substituting the corresponding starting materials in the above methods, one can prepare other azacyclic compounds wherein n is 2,3,4, and 5 to produce the analogs of the above specifically named compounds.

Formulations

I. Tablet Formulations

Formulation and Method of Manufacture for

| Coated Tablets: | mg-core |
|---|---|
| Threo-1-benzhydryl-2-(α-hydroxybenzyl)-azetidine hydrochloride | 25 |
| Lactose | 66 |
| Dicalcium Phosphate | 40 |
| Sodium Lauryl Sulfate | 10 |
| Polyvinylpyrrolidone | 10 |
| Water 50 ml/1000 cores | |
| Corn Starch | 20 |

| Dry | mg - core |
|---|---|
| Sodium Lauryl Sulfate | 2 |
| Magnesium Stearate | 2 |
| Tablet Weight | 175 |

Procedure:

Mix the threo-1-benzhydryl-2-α-(hydroxybenzyl)azetidine hydrochloride with the lactose, dicalcium phosphate, and sodium lauryl sulfate. Screen the above mixture through a No. 60 (US Standard) screen and granulate with an aqueous solution containing polyvinylpyrrolidone. Add additional water, if necessary, to bring powders to a pasty mass. Add corn starch and continue mixing until uniform granules are formed. Pass through a No. 10 (US Standard) screen, tray and dry in oven at 100° C for 12 to 14 hours. Reduce the dried granulation through a No. 16 (US Standard) screen, add sodium lauryl sulfate and magnesium sulfate, mix and compress into desired shape on a tablet machine.

Coating:

Treat the above cores with a lacquer and dust with talc to prevent moisture absorption. Add sub-coat layers to round out the core. Apply a sufficient number of lacquer coats to make the core enteric. Apply additional sub-coats and smoothing coats to completely round out and smooth the tablet. Apply color coats until desired shade is obtained. After drying, polish the coated tablets to give the tablets an even gloss.

II. Capsule Formulations

| Formula: | m.g./capsule |
|---|---|
| Erythro-1-benzhydryl-2-(α-aminobenzyl)-azetidine | 70 |
| Sodium Lauryl Sulfate | 20 |
| Lactose | 34 |
| Magnesium Stearate | 76 |
| | 200 |

Procedure:

Mix together erythro-1-benzhydryl-2-(α-aminobenzyl)azetidine, propionic acid, lauryl sulfate and lactose. Pass through a No. 80 (US Standard) screen. Add magnesium stearate, mix and encapsulate into the proper size two-piece gelatin capsule.

Variations of the above compositions, formulations and processes for the utilization thereof are obvious to those skilled in the art.

We claim:

1. A compound of the formula

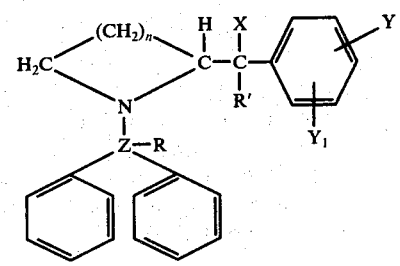

wherein
$n$ is an integer from 1 to 5;
R and R' are independently selected from the group consisting of hydrogen and alkyl of 1–4 carbon atoms;
X is selected from the group consisting of hydrogen, $OR_2$ and $NR_1R_3$;
$R_1$ is hydrogen, alkyl of 1–4 carbon atoms, phenyl lower alkyl,

and

wherein $R_4$ is alkyl of 1–4 carbon atoms, phenyl, or phenyl lower alkyl.
$R_2$ is hydrogen, alkyl of 1–4 carbon atoms, lower alkanoyl, benzoyl or pheyl alkyl of 1–4 carbon atoms;
$R_3$ is hydrogen, alkyl of 1–4 carbon atoms and phenyl lower alkyl;
Y and $Y_1$ are independently selected from the group consisting of hydrogen, halogen, hydroxy, lower alkoxy and trifluoromethyl;
Z is a $C_1$–$C_2$ alkylene group, and the pharmaceutically acceptable salts thereof.
2. A compound of claim 1 wherein $n$ is 1.
3. A compound of claim 1 wherein Z is methylene.
4. A compound of claim 1 wherein R is hydrogen.
5. A compound of claim 1 wherein X is hydroxy.
6. A compound of claim 1 wherein X is hydrogen.
7. A compound of claim 1 wherein X is amino.
8. A compound of claim 7 wherein Y is halogen or trifluoromethyl.
9. A compound of claim 8 wherein $n$ is 1.
10. The compound of claim 9 which is erythro-1-benzhydryl-2-(α-amino-m-trifluoromethylbenzyl)azetidine.
11. The compound of claim 9 which is threo-1-benzhydryl-2-(α-amino-m-trifluoromethylbenzyl)azetidine.
12. The compound of claim 3 which is 1-benzhydryl-2-benzylazetidine.
13. The compound of claim 3 which is 1-benzhydryl-2-benzylpyrrolidine.
14. The compound of claim 5 which is threo-1-benzhydryl-2-(α-hydroxybenzyl)azetidine.
15. The compound of claim 5 which is erythro-1-benzhydryl-2-(α-hydroxybenzyl)azetidine.
16. The compound of claim 7 which is threo-1-benzhydryl-2-(α-aminobenzyl)azetidine.
17. The compound of claim 7 which is erythro-1-benzhydryl-2-(α-aminobenzyl)azetidine.

* * * * *

UNITED STATES PATENT OFFICE
CERTIFICATE OF CORRECTION

Patent No. 4,052,383          Dated  October 4, 1977

Inventor(s) Elijah H. Gold and Daniel M. Solomon

It is certified that error appears in the above-identified patent and that said Letters Patent are hereby corrected as shown below:

Column 8, line 13, "reaction (n) may" should read --- reaction (h) may ---. Column 15, line 6, "other. Wash the" should read --- ether. Wash the ---; line 35, "on equivalent" should read --- one equivalent ---; line 61, "-amino_/azetidine" should read --- amino)benzyl_/azetidine ---. Column 20, lines 20-38, $R_1$ is hydrogen, alkyl of 1-4 carbon atoms, phenyl lower alkyl, $$-\overset{O}{\underset{\|}{C}}-R_4 \text{ and } -\overset{O}{\underset{\underset{O}{\|}}{\overset{\|}{S}}}-R_4$$

wherein $R_4$ is alkyl of 1-4 carbon atoms, phenyl, or phenyl lower alkyl. $R_2$ is hydrogen, alkyl of 1-4 carbon atoms, lower alkanoyl, benzoyl or pheyl alkyl of 1-4 carbon atoms; $R_3$ is hydrogen, alkyl of 1-4 carbon atoms and phenyl lower alkyl;" should read --- $R_1$ is hydrogen, alkyl of 1-4 carbon atoms, phenyl alkyl of 1-4 carbon atoms, $$-\overset{O}{\underset{\|}{C}}-R_4$$

and

UNITED STATES PATENT OFFICE
CERTIFICATE OF CORRECTION

Patent No. 4,052,383        Dated October 4, 1977

Inventor(s) Elijah H. Gold and Daniel M. Solomon

It is certified that error appears in the above-identified patent and that said Letters Patent are hereby corrected as shown below:

$$\overset{O}{\underset{O}{\overset{\|}{\underset{\|}{S}}}}-R_4$$ wherein $R_4$ is alkyl of 1-4 carbon atoms, phenyl, or phenyl alkyl of 1-4 carbon atoms. $R_2$ is hydrogen, alkyl of 1-4 carbon atoms, lower alkanoyl, benzoyl or phenyl alkyl of 1-4 carbon atoms; $R_3$ is hydrogen, alkyl of 1-4 carbon atoms and phenyl alkyl of 1-4 carbon atoms; ---

Signed and Sealed this

Twenty-ninth Day of August 1978

[SEAL]

Attest:

RUTH C. MASON
*Attesting Officer*

DONALD W. BANNER
*Commissioner of Patents and Trademarks*